US007053020B2

(12) United States Patent
De Boer et al.

(10) Patent No.: US 7,053,020 B2
(45) Date of Patent: May 30, 2006

(54) CATALYST SYSTEMS FOR ETHYLENE OLIGOMERISATION TO LINEAR ALPHA OLEFINS

(75) Inventors: Eric Johannes Maria De Boer, Amsterdam (NL); Marijke De Boer-Wildschut, Amsterdam (NL); Harry Van Der Heijden, Amsterdam (NL); Arie Vah Zon, Amsterdam (NL)

(73) Assignee: Shell Oil Company, Houston, TX (US)

( * ) Notice: Subject to any disclaimer, the term of this patent is extended or adjusted under 35 U.S.C. 154(b) by 120 days.

(21) Appl. No.: 10/668,592

(22) Filed: Sep. 23, 2003

(65) Prior Publication Data

US 2004/0116758 A1 Jun. 17, 2004

(30) Foreign Application Priority Data

Sep. 25, 2002 (EP) .................. 02256666

(51) Int. Cl.
*B01J 31/22* (2006.01)
*C08F 4/44* (2006.01)

(52) U.S. Cl. ............... 502/155; 502/167; 502/168; 526/161; 526/171; 526/172; 556/138

(58) Field of Classification Search .............. 502/155, 502/167, 168; 526/161, 171, 172; 556/138
See application file for complete search history.

(56) References Cited

U.S. PATENT DOCUMENTS

| 4,728,583 | A | 3/1988 | Yamazaki et al. | 428/690 |
|---|---|---|---|---|
| 4,912,333 | A | 3/1990 | Roberts et al. | 250/487.1 |
| 4,944,026 | A | 7/1990 | Arakawa et al. | 250/484.1 |
| 5,151,604 | A | 9/1992 | Kohda et al. | 250/484.1 |
| 5,318,935 | A | 6/1994 | Canich et al. | 502/117 |
| 5,726,115 | A | 3/1998 | Horton et al. | 502/152 |
| 5,830,629 | A | 11/1998 | Vizard et al. | 430/523 |
| 5,852,145 | A | 12/1998 | McLain et al. | 526/133 |
| 5,888,647 | A | 3/1999 | Yamane | 428/338 |
| 5,905,014 | A | 5/1999 | Van de Bergh | 430/139 |
| 5,955,555 | A | 9/1999 | Bennett | 526/133 |
| 6,002,034 | A | 12/1999 | McLain et al. | 556/34 |
| 6,063,881 | A | 5/2000 | Bennett | 526/161 |
| 6,103,946 | A | 8/2000 | Brookhart, III et al. | 585/523 |
| 6,150,482 | A | 11/2000 | Brookhart et al. | 526/161 |
| 6,214,761 | B1 | 4/2001 | Bennett | 502/117 |
| 6,232,259 | B1 | 5/2001 | Ittel et al. | 502/155 |
| 6,265,500 | B1 | 7/2001 | Debras | 526/65 |
| 6,310,153 | B1 | 10/2001 | Ittel et al. | 526/172 |
| 6,395,668 | B1 | 5/2002 | van Baar et al. | 502/123 |
| 6,407,188 | B1 | 6/2002 | Guan et al. | 526/113 |
| 6,414,098 | B1 | 7/2002 | Engehausen et al. | 526/161 |
| 6,417,364 | B1 | 7/2002 | Lenges | 546/12 |
| 6,423,848 | B1 | 7/2002 | Bennett | 546/329 |
| 6,432,862 | B1 | 8/2002 | Bennett | 502/117 |
| 6,441,117 | B1 | 8/2002 | Cameron | 526/352 |
| 6,451,939 | B1 | 9/2002 | Britovsek et al. | 526/161 |
| 6,455,660 | B1 | 9/2002 | Clutton et al. | 526/352 |
| 6,458,739 | B1 | 10/2002 | Kimberley et al. | 502/155 |
| 6,458,905 | B1 | 10/2002 | Schmidt et al. | 526/172 |
| 6,461,994 | B1 | 10/2002 | Gibson et al. | 502/155 |
| 6,462,152 | B1 | 10/2002 | Berardi et al. | 526/75 |
| 6,462,155 | B1 | 10/2002 | Okuda | 526/161 |
| 6,465,386 | B1 | 10/2002 | Maddox et al. | 502/155 |
| 6,472,341 | B1 | 10/2002 | Kimberley et al. | 502/155 |
| 6,479,601 | B1 | 11/2002 | Kerns et al. | 526/161 |
| 6,489,497 | B1 | 12/2002 | Brookhart, III et al. | 556/138 |
| 6,521,329 | B1 | 2/2003 | Aylward et al. | 428/212 |
| 6,534,691 | B1 | 3/2003 | Culver et al. | 582/527 |
| 6,545,108 | B1 | 4/2003 | Moody et al. | 526/161 |
| 6,548,672 | B1 | 4/2003 | Gibson et al. | 546/12 |
| 6,555,723 | B1 | 4/2003 | Schiffino | 585/521 |
| 6,559,091 | B1 | 5/2003 | Moody et al. | 502/167 |
| 6,559,252 | B1 | 5/2003 | Horton et al. | 526/160 |
| 6,583,237 | B1 | 6/2003 | Imuta et al. | 526/89 |
| 6,605,677 | B1 | 8/2003 | Lavoie et al. | 526/161 |
| 6,677,267 | B1 | 1/2004 | Berardi et al. | 502/155 |
| 6,683,141 | B1 | 1/2004 | Gibson et al. | 526/161 |
| 6,683,187 | B1 | 1/2004 | De Boer et al. | 546/345 |
| 6,706,891 | B1 | 3/2004 | Ponasik | 548/523 |
| 6,710,006 | B1 | 3/2004 | De Boer et al. | 502/155 |
| 6,740,715 | B1 | 5/2004 | Brookhart, III et al. | 526/161 |
| 6,825,297 | B1* | 11/2004 | Devore et al. | 526/172 |
| 6,838,540 | B1 | 1/2005 | Mitani et al. | 526/348 |
| 2001/0000519 | A1 | 4/2001 | Bennett | 526/329 |
| 2001/0016634 | A1 | 8/2001 | Ittel et al. | 526/172 |
| 2002/0013431 | A1 | 1/2002 | Bennett | 526/90 |

(Continued)

FOREIGN PATENT DOCUMENTS

EP 0 308 728 3/1989

(Continued)

OTHER PUBLICATIONS

U.S. Appl. No. 09/964,714, filed Sep. 27, 2001, De Boer et al.

(Continued)

*Primary Examiner*—Robert D. Harlan

(57) ABSTRACT

A catalyst system comprising:
(a) one or more bisarylimino pyridine iron or cobalt catalysts;
(b) a first co-catalyst compound which is selected from aluminium alkyls, aluminoxanes, and mixtures thereof; and
(c) a second co-catalyst compound which comprises one or more compounds of the formula $ZnR'_2$ wherein each R', which may be the same or different, is selected from hydrogen, optionally substituted $C_1$–$C_{20}$ hydrocarbyl, phenyl, Cl, Br, I, SR", $NR''_2$, OH, OR", CN, NC wherein R", which within the same molecule may the same or different, is $C_1$–$C_{20}$ hydrocarbyl.

21 Claims, No Drawings

U.S. PATENT DOCUMENTS

| | | | |
|---|---|---|---|
| 2002/0016425 A1 | 2/2002 | De Boer et al. | 526/172 |
| 2002/0016521 A1 | 2/2002 | Culver et al. | 585/527 |
| 2002/0019575 A1 | 2/2002 | Schiffino | 585/520 |
| 2002/0028941 A1 | 3/2002 | De Boer et al. | 546/167 |
| 2002/0035031 A1 | 3/2002 | Berardi et al. | 502/171 |
| 2002/0128409 A1 | 9/2002 | De Boer et al. | 526/172 |
| 2003/0036615 A1 | 2/2003 | Brookhart, III et al. | 526/161 |
| 2003/0045752 A1 | 3/2003 | De Boer et al. | 562/545 |
| 2003/0050494 A1 | 3/2003 | Brookhart, III et al. | 556/138 |
| 2003/0119921 A1 | 6/2003 | De Boer et al. | 518/715 |
| 2003/0125195 A1 | 7/2003 | Britovsek et al. | 502/117 |
| 2003/0144514 A1 | 7/2003 | De Boer et al. | 546/12 |
| 2003/0195110 A1 | 10/2003 | Moody et al. | 502/150 |
| 2003/0225228 A1 | 12/2003 | Moody et al. | 526/172 |
| 2004/0116758 A1 | 6/2004 | De Boer et al. | 585/521 |
| 2005/0014983 A1 | 1/2005 | De Boer et al. | 585/511 |

FOREIGN PATENT DOCUMENTS

| | | |
|---|---|---|
| EP | 1125928 A1 | 8/2001 |
| EP | 1125987 | 8/2001 |
| EP | 1127987 A1 | 8/2001 |
| EP | 0 927 201 B1 | 4/2004 |
| JP | 04325504 | 11/1992 |
| RU | 418462 | 9/1974 |
| WO | WO 92/12162 | 7/1992 |
| WO | WO 96/27439 | 9/1996 |
| WO | WO 98/27124 | 6/1998 |
| WO | WO 99/02472 | 1/1999 |
| WO | WO 99/12981 | 3/1999 |
| WO | WO 99/50273 | 10/1999 |
| WO | WO 99/51550 | 10/1999 |
| WO | 99/62967 | 12/1999 |
| WO | WO 00/08034 | 2/2000 |
| WO | WO 00/15646 | 3/2000 |
| WO | WO 00/20427 | 4/2000 |
| WO | WO 00/24788 | 5/2000 |
| WO | WO 00/50470 | 8/2000 |
| WO | WO 01/36379 A1 | 5/2001 |
| WO | WO 01/58874 A1 | 8/2001 |
| WO | WO 02/00339 A2 | 1/2002 |
| WO | WO 02/06192 A1 | 1/2002 |
| WO | WO 02/12151 A1 | 2/2002 |
| WO | WO 02/28805 A2 | 4/2002 |
| WO | WO 03/000628 A1 | 1/2003 |
| WO | WO 03/011876 A1 | 2/2003 |

OTHER PUBLICATIONS

U.S. Appl. No. 10/208,535, filed Jul. 30, 2002, De Boer et al.

U.S. Appl. No. 10/739,715, filed Dec. 18, 2003, De Boer et al.

U.S. Appl. No. 10/320,213, filed Dec. 16, 2002, De Boer et al.

D. van Leusen and B. Hesen, Organometallics, 2001, 20, pp. 224-226.

Chemical Abstracts, vol. 134, Columbus, Ohio, US; Abstract No. 231149, Radecka-Paryzek, W. et al., "Metal-Ion-Dispersed Synthesis of Homo- and Heteronuclear Dimetallic Schiff Base Podates," Pol. J. Chem. 2001, 75(1), pp. 35-42.

D. Vogt, Oligomerisation of ethylene to higher alpha-olefins in Applied Homogeneous Catalysis with organometallic Compounds, Ed. B. Comils, W. A. Herrmann, $2^{nd}$ [1]Edition, vol. 1, Ch. 2.3.1.1, p. 240-253, Wiley-VCH 2002).

Angew. Chem. Int. ED. 2002, 41, No. 3, "Iron-Catalyzed Polyethylene Chain Growth on Zinc: Linear α-Olefins With a Poisson Distribution," by George J. P. Britovsek, et al., pp. 489-491.

"Late Metal Catalysts for Ethylene Homo- and Copolymerization," by Steven D. Ittel et al., Chemical Reviews, American Chemical Society, Easton, US, vol. 100, No. 4, 2000, pp. 1169-1203.

Oligomerisation of Ethylene by Bis(imino)pydidyliron and -cobalt Complexes, by George J. P. Britovsek et al., Chemistry—A European Journal, VCH Publishers, US, vol. 6, No. 12, 2000, pp. 2221-2231.

"Novel Olefin Polymerization Catalysts Based on Iron and Cobalt," by George J. P. Britovsek et al., Chemical Communications-Chemcom, Roayl Society of Chemistry, GB, No. 7, 1998, pp. 849-850.

"Olefin Polymerization with [{bis(imino)pyridyl}CO" $Cl_2$]: Generation of the Active Species Involves $CO^{1**}$, by Martijn Kooistra et al., Angewandte Chemie. International Edition, WILEY-VCH, Weinheim, DE, vol. 40, No. 24, Dec. 17, 2001, pp. 4719-4722.

"The Nature of the Active Species in Bis(imino)pyridyl Cobalt Ethylene Polymerisation Catalysts," by Vernon C. Gibson, et al., Chemical Communications-Chemcom, Royal Society of Chemistry, GB. No. 21, 2001, pp. 2252-2253.

"Iron-Based Catalysts with Exceptionally High Activities and Selectivities for Oligomerization of Ethylene to Linear α-Olefins," by Brooke L. Small et al., Journal of the American Chemical Society, Washington, DC, vol. 120, No. 28, Jul. 22, 1998, pp. 7143-7144.

Paul E. Figgins et al., "Complexes of Iron (II), Corbalt (II) and Nickel (II) with Biacetyl-bis-methylimine, 2-Pyridinal-methylimine and 2,6-Pyridindial-bis-methylimine," J. Am. Chem. Soc. (1960) vol. 82, pp. 820-824.

Francis Lions et al., "Tridentate Chelate Compounds. I," J. Am Chem. Soc. (1957), vol. 79, pp. 2733-2738.

"Novel, Highly Active Iron and Cobalt Catalysts for Olefin Polymerization," by Allsion M. A. Bennett, *Chemtech* Jul. 1999, pp. 24-28.

"Polymerization of Propylene by a New Generation of Iron Catalysts: Mechanisms of Chain Initiation, Propagation, and Termination," by Brooke L. Small and Maurice Brookhart, Macromolecules, vol. 32, No. 7, 1999, pp. 21210-2130.

"Metal-Ion-Directed Sythesis of Homo-and Heteronuclear Dimetallic Schiff Base Prodates," by W. Radecka-Paryzek, M. T. Kaczmarek, and E. Luks, Polish J. Chem., 75, (2001) pp. 35-42.

2005/159601 7/2005 De Boer et al. 546 2

"1,1-Diisocyanoterrocene and a Covenient Synthesis of Ferrocenylamine, " by Daan van Leusen and Bart Hessen, Organometallics, 2001, pp. 224-226.

U.S. Appl No. 11/080170, filed Mar. 15, 2005, De Boer et al.

* cited by examiner

CATALYST SYSTEMS FOR ETHYLENE OLIGOMERISATION TO LINEAR ALPHA OLEFINS

FIELD OF THE INVENTION

The present invention relates to catalyst systems for ethylene oligomerisation to linear alpha olefins in high yield and very high selectivity and a process for preparing said linear alpha olefins.

BACKGROUND OF THE INVENTION

Various processes are known for the production of higher linear alpha olefins (for example D. Vogt, *Oligomerisation of ethylene to higher α-olefins* in Applied Homogeneous Catalysis with Organometallic Compounds Ed. B. Cornils, W. A. Herrmann, $2^{nd}$ Edition, Vol. 1, Ch. 2.3.1.3, page 240–253, Wiley-VCH 2002). These commercial processes afford either a Poisson or Schulz-Flory oligomer product distribution.

In order to obtain a Poisson distribution, no chain termination must take place during oligomerisation. However, in contrast, in a Schulz-Flory process, chain termination does occur and is independent from chain length. The Ni-catalysed ethylene oligomerisation step of the Shell Higher Olefins Process (SHOP) is a typical example of a Schulz-Flory process.

In a Schulz-Flory process, a wide range of oligomers are typically made in which the fraction of each olefin can be determined by calculation on the basis of the so-called K-factor. The K-factor, which is indicative of the relative proportions of the product olefins, is the molar ratio of $[C_{n+2}]/[C_n]$ calculated from the slope of the graph of log $[C_n$ mol %] versus n, where n is the number of carbon atoms in a particular product olefin. The K-factor is by definition the same for each n. By ligand variation and adjustment of reaction parameters, the K-factor can be adjusted to higher or lower values. In this way, the process can be operated to produce a product slate with an optimised economic benefit.

Since demand for the $C_6$–$C_{18}$ fraction is much higher than for the $C_{>20}$ fraction, processes are geared to produce the lower carbon number olefins. However, the formation of the higher carbon number olefins is inevitable, and, without further processing, the formation of these products is detrimental to the profitability of the process. To reduce the negative impact of the higher carbon number olefins and of the low value $C_4$ fraction, additional technology has been developed to reprocess these streams and convert them into more valuable chemicals such as internal $C_6$–$C_{18}$ olefins, as is practised in the Shell Higher Olefins Process.

However, this technology is expensive both from an investment and operational point of view and consequently adds additional cost. Therefore considerable effort is directed to keep the production of the higher carbon numbered olefins to the absolute minimum, i.e. not more than inherently associated with the Schulz-Flory K-factor.

In this regard a number of published patent applications describe catalyst systems for the polymerisation or oligomerisation of 1-olefins, in particular ethylene, which contain nitrogen-containing transition metal compounds. See, for example, the following patent applications which are incorporated herein by reference in their entirety: WO 92/12162, WO 96/27439, WO 99/12981, WO 00/50470, WO 98/27124, WO 99/02472, WO 99/50273, WO 99/51550, EP-A-1,127,987, WO 02/12151, WO 02/06192, WO 99/12981, WO 00/24788, WO 00/08034, WO 00/15646, WO 00/20427, WO 01/58874 and WO 03/000628.

In particular, recently published Shell applications WO01/58874, WO02/00339, WO02/28805 and WO 03/011876, all of which are incorporated herein by reference in their entirety, disclose novel classes of catalysts based on bis-imine pyridine iron compounds which are highly active in the oligomerisation of olefins, especially ethylene and which produce linear alpha olefins in the $C_6$–$C_{30}$ range with a Schulz-Flory distribution, said linear alpha olefins being of high purity.

There is still a need however for improving the selectivity of the linear alpha olefins in the oligomerisation processes described in the prior art.

It is known to use a co-catalyst such as an aluminium alkyl or aluminoxane in conjunction with an olefin polymerization catalyst. It has now surprisingly been found that replacement of a portion of the aluminium alkyl or aluminoxane co-catalyst with one or more particular zinc compounds, such as $ZnEt_2$, results in an improvement in the selectivity for linear alpha-olefins in the above mentioned oligomerisation process catalysed by bisarylimine pyridine iron compounds. At the same time, the amount of unwanted by-products such as internal and branched olefins and dienes, is reduced.

Angew. Chem. Int. Ed. 2002, 41, No. 3, pages 489–491, entitled "Iron-Catalyzed Polyethylene Chain Growth on Zinc: Linear alpha-olefins with a Poisson Distribution" by George J. P. Britovsek, Steven A. Cohen, Vernon C. Gibson, Peter J. Maddox, and Martin van Meurs, discloses a chain growth process on zinc, catalysed by a bis(imino)pyridine iron catalyst. However, analysis of the polymer produced by the reaction after hydrolysis revealed a fully saturated linear alkane product, rather than an alpha-olefin product. In order to obtain an alpha-olefin this reference describes a nickel-catalyzed displacement of the grown alkyl chain, in the presence of ethylene to regenerate diethyl zinc. The distribution of alpha olefins produced is said to be a Poisson distribution rather than a Schulz-Flory distribution.

SUMMARY OF THE INVENTION

The present invention provides a catalyst system comprising:

(a) one or more bisarylimino pyridine iron or cobalt catalysts;

(b) a first co-catalyst compound which is selected from aluminium alkyls, aluminoxanes, and mixtures thereof; and (c) a second co-catalyst compound which comprises one or more compounds of the formula $ZnR'_2$ wherein each R', which may be the same or different, is selected from hydrogen, optionally substituted $C_1$–$C_{20}$ hydrocarbyl, phenyl, F, Cl, Br, I, SR", NR"$_2$, OH, OR", CN, NC wherein R", which within the same molecule may be the same or different, is optionally substituted $C_1$–$C_{20}$ hydrocarbyl.

In a further aspect of the present invention there is provided a process for the production of linear alpha-olefins comprising reacting ethylene under oligomerisation conditions in the presence of an effective amount of the catalyst system described herein.

DETAILED DESCRIPTION OF THE INVENTION

A first essential component in the catalyst system of the present invention is one or more bisarylimino pyridine iron or cobalt catalysts. Any bisarylimino pyridine iron or cobalt catalyst suitable for use in ethylene oligomerisation reactions for producing linear alpha olefins may be used herein.

Suitable bisarylimino pyridine iron or cobalt catalysts for use herein include, but are not limited to, bis-ariliminepyridine $MX_n$ complexes and/or [bis-aryliminepyridine $MY_p \cdot L_b^+][NC^-]_q$ complexes, said bis-aryliminepyridine complexes comprising a bisarylimine pyridine ligand, wherein M is a metal atom selected from Fe or Co, n is 2 or 3, and X is halide, optionally substituted hydrocarbyl, alkoxide, amide or hydride, Y is a ligand which may insert an olefin, $NC^-$ is a non-coordinating anion, p+q is 2 or 3, matching the formal oxidation of said metal atom; L is a neutral Lewis donor molecule; b is 0, 1 or 2. Bisarylimino pyridine iron or cobalt catalysts of this type are disclosed in WO01/58874, WO02/00339, WO02/28805 and WO 03/011876, all of which are incorporated herein by reference in their entirety.

Particularly suitable bisarylimine pyridine ligands for use in the catalyst systems herein include those having the formula (I) below:

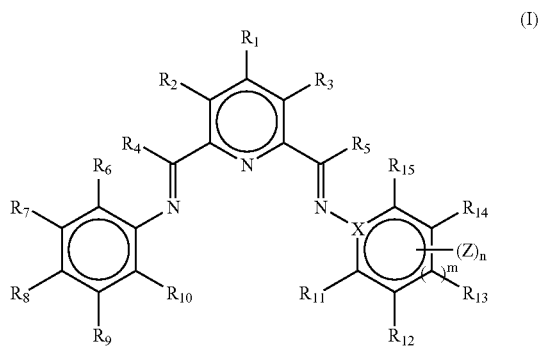

(I)

wherein X is carbon or nitrogen,
n is 0 or 1,
m is 0 or 1,
Z is a π-coordinated metal fragment,
$R_1$–$R_5$, $R_7$–$R_9$ and $R_{12}$–$R_{14}$ are each, independently, hydrogen, optionally substituted hydrocarbyl, an inert functional group, or any two of $R_1$–$R_3$, $R_7$–$R_9$ and $R_{12}$–$R_{14}$ vicinal to one another taken together may form a ring; $R_6$ is hydrogen, optionally substituted hydrocarbyl, an inert functional group, or taken together with $R_7$ or $R_4$ to form a ring; $R_{10}$ is hydrogen, optionally substituted hydrocarbyl, an inert functional group, or taken together with $R_9$ or $R_4$ to form a ring; $R_{11}$ is hydrogen, optionally substituted hydrocarbyl, an inert functional group, or taken together with $R_5$ or $R_{12}$ to form a ring; and $R_{15}$ is hydrogen, optionally substituted hydrocarbyl, an inert functional group, or taken together with $R_5$ or $R_{14}$ to form a ring.

In the present invention certain terms are used as follows:

The term "π-coordinated metal fragment" in relation to the group Z means that the Z group together with the ring containing the X atom represents a metallocene moiety or a sandwich or metal-arene complex which can be optionally substituted. The Z group contains a metal atom which is π-coordinated to the aromatic ring containing the X atom. The Z group can also contain one or more ligands which are coordinated to the metal atom, such as, for example (CO) ligands, such that the Z group forms the metal fragment Fe $(CO)_x$. Preferably, however, the Z group contains an optionally substituted aromatic ring which is π-coordinated to the metal. Said optionally substituted aromatic ring can be any suitable monocyclic or polycyclic, aromatic or heteroaromatic ring having from 5 to 10 ring atoms, optionally containing from 1 to 3 heteroatoms selected from N, O and S. Preferably the aromatic ring is a monocyclic aromatic ring containing from 5 to 6 carbon atoms, such as phenyl and cyclopentadienyl. Non-limiting examples of combinations of aromatic hydrocarbon rings containing an X atom and π-coordinated metal fragments include ferrocene, cobaltocene, nickelocene, chromocene, titanocene, vanadocene, bis-benzene chromium, bis-benzene titanium and similar heteroarene metal complexes, mono-cationic arene manganese tris carbonyl, arene ruthenium dichloride.

The term "Hydrocarbyl group" in relation to the $R^1$ to $R^{15}$ groups of formula (I) above means a group containing only carbon and hydrogen atoms. Unless otherwise stated, the number of carbon atoms is preferably in the range from 1 to 30, especially from 1 to 6. The hydrocarbyl group may be saturated or unsaturated, aliphatic, cycloaliphatic or cycloaromatic (e.g. phenyl), but is preferably aliphatic. Suitable hydrocarbyl groups include primary, secondary and tertiary carbon atom groups such as those described below.

In the present invention, the phrase "optionally substituted hydrocarbyl" in relation to the $R^1$ to $R^{15}$ groups of formula (I) above is used to describe hydrocarbyl groups optionally containing one or more "inert" heteroatom-containing functional groups. By "inert" is meant that the functional groups do not interfere to any substantial degree with the (co-) oligomerisation process. Non-limiting examples of such inert groups are fluoride, chloride, silanes, stannanes, ethers, alkoxides and amines with adequate steric shielding, all well-known to those skilled in the art. Some examples of such groups include methoxy, trimethylsiloxy and eicosanoxy. Said optionally substituted hydrocarbyl may include primary, secondary and tertiary carbon atom groups of the nature described below.

The term "inert functional group" in relation to the $R^1$ to $R^{15}$ groups of formula (I) above means a group other than optionally substituted hydrocarbyl which is inert under the oligomerisation process conditions herein. By "inert" is meant that the functional group does not interfere to any substantial degree with the (co-) oligomerisation process. Examples of inert functional groups suitable for use herein include halide, ethers, and amines such as tertiary amines, especially fluorine and chlorine.

The term "Primary carbon atom group" as used herein means a —$CH_2$—R group wherein R is selected from hydrogen, an optionally substituted hydrocarbyl, or an inert functional group. Examples of suitable primary carbon atom groups include, but are not limited to, —$CH_3$, —$C_2H_5$, —$CH_2Cl$, —$CH_2OCH_3$, —$CH_2N(C_2H_5)_2$ and —$CH_2Ph$. Preferred primary carbon atom groups for use herein are those wherein R is selected from hydrogen or a $C_1$–$C_6$ unsubstituted hydrocarbyl, preferably wherein R is hydrogen or a $C_1$–$C_3$ alkyl.

The term "Secondary carbon atom group" as used herein means a —$CH(R)_2$ group wherein each R is independently selected from an optionally substituted hydrocarbyl or an inert functional group. Alternatively, the two R groups may together represent a double bond moiety, e.g. =$CH_2$, or a cycloalkyl group. Examples of secondary carbon atom groups include, but are not limited to, —CH(CH$_3$)$_2$, —CHCl$_2$, —CHPh$_2$, —CH═CH$_2$ and cyclohexyl. Preferred secondary carbon atom groups for use herein are those in which R is a C$_1$–C$_6$ unsubstituted hydrocarbyl, preferably a C$_1$–C$_3$ alkyl.

The term "Tertiary carbon atom group" as used herein means a —C(R)$_3$ group wherein each R is independently selected from an optionally substituted hydrocarbyl or an inert functional group. Alternatively, the three R groups may together represent a triple bond moiety, e.g. —C≡CPh, or a ring system containing tertiary carbon atoms such as adamantyl derivatives. Examples of tertiary carbon atom groups include, but are not limited to, —C(CH$_3$)$_3$, —CCl$_3$, —C≡CPh, 1-Adamantyl and —C(CH$_3$)$_2$(OCH$_3$). Preferred tertiary carbon atom groups for use herein are those wherein each R is a C$_1$–C$_6$ unsubstituted hydrocarbyl group, preferably wherein each R is a C$_1$–C$_3$ alkyl group, more preferably wherein each R is methyl. In the case wherein each R is a methyl group, the tertiary carbon atom group is tert-butyl.

By a "ligand which may insert an olefin" is meant a ligand which is coordinated to a metal ion into which bond an ethylene molecule or an alpha-olefin may be inserted to initiate or propagate a (co-)oligomerisation reaction. In [bis-aryliminepyridine MY$_p$.L$_b$$^+$][NC$^-$]$_q$ complexes according to the present invention, Y may be hydride, alkyl or any other anionic ligand which may insert an olefin.

By "non-coordinating anion" is meant an anion which does not substantially coordinate to the metal atom M. Non-coordinating anions (NC$^-$) that may be suitably employed include bulky anions such as tetrakis [3,5-bis (trifluoromethyl)phenyl]borate (BAF$^-$), (C$_6$F$_5$)$_4$B$^-$, and anions of alkylaluminium compounds including R$_3$AlX$^-$, R$_2$AlClX$^-$, RAlCl$_2$X$^-$, and "RAlOX$^-$", wherein R is hydrogen, optionally substituted hydrocarbyl or an inert functional group, and X is halide, alkoxide or oxygen.

It will be appreciated by those skilled in the art that within the boundary conditions hereinbefore described, substituents R$_{1-15}$ may be readily selected to optimise the performance of the catalyst system and its economical application.

In one preferred embodiment of the invention, the bisarylimino pyridine metal catalyst is a bisarylimino pyridine iron catalyst.

A preferred bisarylimine ligand for use herein is a ligand of formula (I) wherein X is C, m is 1 and n is 0 such that the ring containing the X atom is a 6-membered aromatic group.

Another preferred bisarylimine ligand for use herein is a ligand of formula (I) wherein X is C, m is 0, n is 1, and the ring containing X together with the Z group is a metallocene group.

Yet another preferred bisarylimine ligand for use herein is a ligand of formula (I) wherein X is N, m is 0, n is 0, such that the ring containing the X atom is a 1-pyrrolyl group.

To restrict the products to oligomers it is preferred that no more than one of R$_6$, R$_{10}$, R$_{11}$ and R$_{15}$ is a tertiary carbon atom group. It is also preferred that not more than two of R$_6$, R$_{10}$, R$_{11}$ and R$_{15}$ is a secondary carbon atom group.

Preferred ligands for use herein include those of formula (I) with the following ortho substituents:
(i) R$_6$, R$_{10}$, R$_{11}$ and R$_{15}$ are each, independently, F or Cl;
(ii) R$_6$ and R$_{10}$ are primary carbon atom groups, R$_{11}$ is H or F and R$_{15}$ is H, F or primary carbon atom group;
(iii) R$_6$ and R$_{10}$ are each, independently, H or F, R$_{11}$ and R$_{15}$ are each, independently, F, Cl or primary carbon atom group;
(iv) R$_6$ is H or F, R$_{10}$ is H, F or primary carbon atom group, R$_{11}$ and R$_{15}$ are primary carbon atom groups;
(v) R$_6$ is a primary or secondary carbon atom group, R$_{10}$ is hydrogen, R$_{11}$ and R$_{15}$ are H, F, Cl, primary or secondary carbon atom groups;
(vi) R$_6$ is tertiary carbon atom group, R$_{10}$ is hydrogen, R$_{11}$ is H, F, Cl, primary carbon atom group and R$_{15}$ is H or F;
(vii) R$_6$ is tertiary carbon atom group, R$_{10}$ is primary carbon atom group, R$_{11}$ and R$_{15}$ are H or F;
(viii) R$_6$ and R$_{10}$ are H, F, Cl, primary carbon atom group, secondary carbon atom group, R$_{11}$ is primary or secondary carbon atom group and R$_{15}$ is H;
(ix) R$_6$ is H, F, Cl, R$_{10}$ is H, F, Cl or primary carbon atom group, R$_{11}$ is tertiary carbon atom group and R$_{15}$ is H;
(x) R$_6$ and R$_{10}$ are H, F or Cl, R$_{11}$ is tertiary carbon atom group, R$_{15}$ is primary carbon atom group.

Particularly preferred ligands for use herein include those of formula (I) wherein R$_1$–R$_3$ are hydrogen and R$_4$ and R$_5$ are methyl, H, benzyl or phenyl, preferably methyl.

Especially preferred ligands for use herein include:— a ligand of formula (I), wherein R$_1$–R$_3$ are hydrogen; R$_4$ and R$_5$ are methyl; R$_6$ and R$_{10}$ are methyl; R$_8$ is methyl or hydrogen, R$_7$ and R$_9$ are hydrogen; R$_{11}$ and R$_{15}$ are hydrogen; R$_{12}$, R$_{13}$, and R$_{14}$ are independently hydrogen, methyl, or tert-butyl; X is C, m is 1, n is 0;

a ligand of formula (I), wherein R$_1$–R$_3$ are hydrogen; R$_4$ and R$_5$ are methyl; R$_6$, R$_8$ and R$_{10}$ are methyl; R$_7$ and R$_9$ are hydrogen; R$_{11}$ is fluorine; and R$_{12}$–R$_{15}$ are hydrogen; and X is C, m is 1 and n is 0;

a ligand of formula (I), wherein R$_1$–R$_3$ are hydrogen; R$_4$ and R$_5$ are methyl; R$_7$–R$_9$ and R$_{12}$–R$_{14}$ are hydrogen; R$_6$, R$_{10}$, R$_{11}$ and R$_{15}$ are fluorine; X is C, m is 1 and n is 0;

a ligand of formula (I), wherein R$_1$–R$_3$ are hydrogen, R$_4$ and R$_5$ are methyl, R$_6$, R$_8$ and R$_{10}$ are methyl, R$_7$ and R$_9$ are hydrogen, m is 1, n is 0, X is C, R$_{11}$, R$_{12}$, R$_{14}$ and R$_{15}$ are hydrogen, R$_{13}$ is methoxy or trimethylsiloxy;

a ligand of formula (I), wherein R$_1$–R$_3$ are hydrogen; R$_4$ and R$_5$ are methyl; R$_6$ and R$_{10}$ are methyl; R$_8$ is methyl or hydrogen, R$_7$ and R$_9$ are hydrogen; R$_{11}$ and R$_{15}$ are hydrogen; R$_{12}$, R$_{13}$, and R$_{14}$ are independently hydrogen, methyl, or fluorine; X is C, m is 1, n is 0;

a ligand of formula (I), wherein R$_1$–R$_3$ are hydrogen; R$_4$ and R$_5$ are methyl, R$_6$, R$_8$ and R$_{10}$ are methyl, R$_7$ and R$_9$ are hydrogen, m is 1, n is 0, X is C, R$_{11}$ and R$_{15}$ are hydrogen, R$_{12}$ and R$_{14}$ are phenyl, R$_{13}$ is methoxy, trimethylsiloxy or eicosanoxy.

In the bis-aryliminepyridine MX$_n$ complex, X may conveniently be halide, preferably chloride.

In a preferred embodiment of the bis-aryliminepyridine MX$_n$ complex, metal atom M is Fe and n is 2. In another preferred embodiment, metal atom M is Fe and n is 3.

A neutral Lewis donor molecule is a compound which may suitably act as a Lewis base, such as ethers, amines, sulphides and organic nitriles, for example, triethylamine or 2,6-di-tert-butylpyridine.

In the [bis-aryliminepyridine MY$_p$.L$_b$$^+$][NC$^-$]$_q$ complex according to the present invention, L may be a neutral Lewis donor molecule capable of being displaced by ethylene, or a vacant coordination site.

In the [bis-aryliminepyridine MY$_p$.L$_b$$^+$][NC$^-$]$_q$ complex according to the present invention, metal atom M is preferably Fe and the formal oxidation state of said metal atom may be 2 or 3.

Co-Catalyst Compounds

A second essential component of the catalyst systems herein is a first co-catalyst compound selected from an aluminium alkyl or aluminoxane. Any aluminium alkyl or aluminoxane suitable for use as a co-catalyst can be used herein. Mixtures of two or more aluminium alkyl and/or aluminoxane compounds may also be used herein. Suitable aluminium alkyl or aluminoxane compounds for use herein include methylaluminoxane (MAO) and modified methylaluminoxane (MMAO). Modified methylaluminoxane is derived from methylaluminoxane with a portion of the methyl groups replaced with other alkyl groups, for example, isobutyl groups. In especially preferred embodiments, the first co-catalyst compound is a modified methylaluminoxane, preferably wherein about 25% of the methyl groups are replaced with isobutyl groups.

A third essential component of the catalyst systems herein is a second co-catalyst compound selected from formula $ZnR'_2$ wherein each R', which may be the same or different, is selected from hydrogen, optionally substituted $C_1$–$C_{20}$ hydrocarbyl, phenyl, F, Cl, Br, I, SR", NR"$_2$, OH, OR", CN, NC wherein R", which within the same molecule may the same or different, is $C_1$–$C_{20}$ hydrocarbyl.

In preferred catalyst systems of the present invention, the second co-catalyst compound is $ZnR'_2$ wherein R' is $C_1$–$C_{20}$ hydrocarbyl, more preferably $C_1$–$C_{20}$ alkyl, even more preferably $C_1$–$C_6$ alkyl. Suitable alkyl groups include methyl, ethyl, propyl, butyl, and the like. It is especially preferred that the R' group is a $C_1$–$C_3$ alkyl, especially ethyl.

The second co-catalyst is particularly valuable in combination with the first co-catalyst for increasing the selectivity of linear alpha olefins in ethylene oligomerization reactions, and decreasing the amount of unwanted by-products such as branched olefins, internal olefins, 2,2-disubstituted olefins, and dienes.

It has been noted that particularly high selectivity of linear alpha olefins is achieved when the molar ratio of the metal of the first co-catalyst to the metal of the second co-catalyst is in the range of from about 5:1 to about 1:5, preferably from about 3:1 to about 1:3, more preferably from about 2:1 to about 1:2 and especially 1:1.

It is possible to add further optional components to the catalyst systems herein, for example, Lewis acids and bases such as those disclosed in WO02/28805.

The catalyst system may be formed by mixing together the iron or cobalt bis-imine pyridine complex or a mixture of an iron or cobalt acetylacetonate salt and the appropriate bis-imine pyridine ligand, first co-catalyst compound, second co-catalyst compound and any optional additional compounds, preferably in a solvent such as toluene or isooctane.

Oligomerisation Reactions

A quantity of the catalyst system is usually employed in the oligomerisation reaction mixture so as to contain from about $10^{-4}$ to about $10^{-9}$ gram atom of metal atom M, in particular of Fe [II] or [III] metal per mole of ethylene to be reacted.

The oligomerisation reaction may be most conveniently conducted over a range of temperatures from about −100° C. to about +300° C., preferably in the range of from about 0° C. to about 200° C., and more preferably in the range of from about 50° C. to about 150° C.

The oligomerisation reaction may be conveniently carried out at a pressure of about 0.01 to about 15 mPa (about 0.1 to about 150 bar(a)), more preferably about 1 to about 10 mPa (about 10 to about 100 bar(a)), and most preferably about 1.5 to about 5 mPa (about 15 to about 50 bar(a)).

The optimum conditions of temperature and pressure used for a particular catalyst system to maximise the yield of oligomer, and to minimise the competing reactions such as dimerisation and polymerisation can be readily established by one skilled in the art.

The conditions of temperature and pressure are preferably selected to yield a product slate with a K-factor within the range of from about 0.40 to about 0.90, most preferably in the range of from about 0.60 to about 0.80. In the present invention, polymerisation is deemed to have occurred when a product slate has a K-factor greater than about 0.9.

The oligomerisation reaction can be carried out in the gas phase or liquid phase, or mixed gas-liquid phase, depending upon the volatility of the feed and product olefins.

The oligomerisation reaction is carried out in the presence of an inert solvent which may also be the carrier for the catalyst and/or feed olefin. Suitable solvents include alkanes, alkenes, cycloalkanes, and aromatic hydrocarbons. For example, solvents that may be suitably used according to the present invention include heptane, isooctane, cyclohexane, benzene, toluene, and xylene.

Reaction times of from about 0.1 to about 10 hours have been found to be suitable, dependent on the activity of the catalyst. The reaction is preferably carried out in the absence of air or moisture.

The oligomerisation reaction may be carried out in a conventional fashion. It may be carried out in a stirred tank reactor, wherein olefin and catalyst or catalyst precursors are added continuously to a stirred tank and reactant, product, catalyst, and unused reactant are removed from the stirred tank with the product separated and the unused reactant and optionally the catalyst recycled back to the stirred tank.

Alternatively, the reaction may be carried out in a batch reactor, wherein the catalyst precursors, and reactant olefin are charged to an autoclave, and after being reacted for an appropriate time, product is separated from the reaction mixture by conventional means, such as distillation.

After a suitable reaction time, the oligomerisation reaction can be terminated by rapid venting of the ethylene in order to deactivate the catalyst system.

The resulting alpha olefins have a chain length of from 4 to 100 carbon atoms, preferably 4 to 30 carbon atoms, and most preferably from 4 to 20 carbon atoms.

Product olefins can be recovered suitably by distillation and further separated as desired by distillation techniques dependent on the intended end use of the olefins.

The present invention will now be illustrated by the following Examples, which should not be regarded as limiting the scope of the present invention in any way.

EXPERIMENTAL

General Procedures and Characterisation

All the operations with the catalyst systems were carried out under nitrogen atmosphere. All solvents used were dried using standard procedures.

Anhydrous toluene (99.8% purity) (ex. Aldrich) was dried over 4 Å molecular sieves (final water content of about 3 ppm).

Ethylene (99.5% purity) was purified over a column containing 4 Å molecular sieves and BTS catalyst (ex. BASF) in order to reduce water and oxygen content to <1 ppm.

The oligomers obtained were characterised by Gas Chromatography (GC), in order to evaluate oligomer distribution using a HP 5890 series II apparatus and the following chromatographic conditions:

Column: HP-1 (cross-linked methyl siloxane), film thickness=0.25 μm, internal diameter=0.25 mm, length 60 m (by Hewlett Packard); injection temperature: 325° C.; detection temperature: 325° C.; initial temperature: 40° C. for 10 minutes; temperature programme rate: 10° C./minute; final temperature: 325° C. for 41.5 minutes; internal standard: n-hexylbenzene.

The yields of the $C_4$–$C_{30}$ olefins were obtained from the GC analysis. The NMR data were obtained at room temperature with a Varian 300 MHz or 400 MHz apparatus.

The catalyst used in the oligomerisation experiments below was 2-[1-(2,4,6-trimethylphenylimino)ethyl]-6-[1-(4-tert-butylphenylimino)ethyl]pyridine iron[II] chloride complex which was prepared according to the method disclosed in WO02/28805 and which has the formula below:

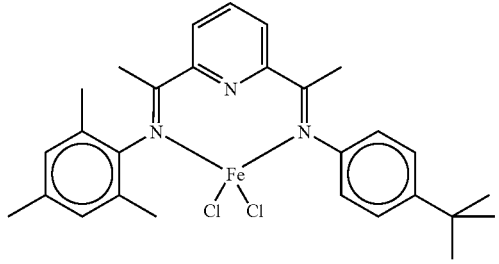

Alternatively the catalyst used in the oligomerisation experiments below was 2,6-bis[1-(2,6-difluorophenylimino)ethyl]pyridine iron[II] chloride complex which was prepared according to the method disclosed in WO02/00339 and which has the formula below:

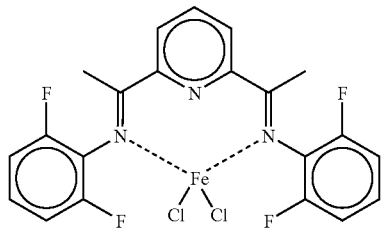

Alternatively the catalyst used in the oligomerisation experiments below was 2-[1-(2,4,6-trimethylphenylimino) ethyl]-6-[1-(3,5-di-tert-butylphenylimino)ethyl]pyridine iron[II] chloride complex which was prepared according to the method described below:

Preparation of 2-[1-(2,4,6-trimethylphenylimino)ethyl]-6-[1-(3,5-di-tert-butylphenylimino)ethyl]pyridine

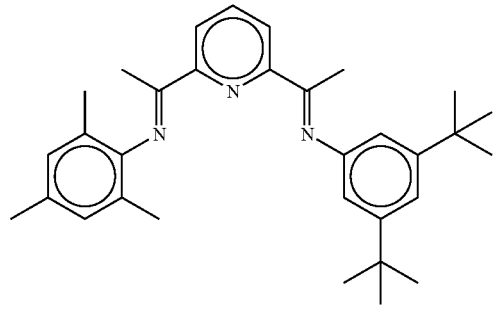

2-[1-(2,4,6-trimethylphenylimino)ethyl]-6-acetylpyridine (1.3 g, 4.64 mmol), prepared according to the method disclosed in WO02/28805, and 3,5-di-tert-butylaniline (1 g, 4.87 mmol) were dissolved in 100 ml of toluene. To this solution, 4 Å molecular sieves were added. After standing for 2 days the mixture was filtered. The solvent was removed in vacuo. The residue was washed with methanol and crystallised from ethanol. Yield 1.1 g (51%) of 2-[1-(2,4,6-trimethylphenylimino) ethyl]-6-[1-(3,5-di-tert-butylphenylimino)ethyl]pyridine. $^1$H-NMR (CDCl$_3$) δ 8.43 (d, 1H, Py-H$_m$), 8.37 (d, 1H, Py-H$_m$), 7.87 (t, 1H, Py-H$_p$), 7.16 (t, 1H, ArH), 6.89 (s, 2H, ArH), 6.69 (d, 2H, ArH), 2.42 (s, 3H, Me), 2.29 (s, 3H, Me), 2.22 (s, 3H, Me), 2.01 (s, 6H, Me), 1.33 (s, 18H, Bu$^t$).

Preparation of 2-[1-(2,4,6-trimethylphenylimino)ethyl]-6-[1-(3,5-di-tert-butylphenylimino)ethyl]pyridine iron[II] Chloride Complex

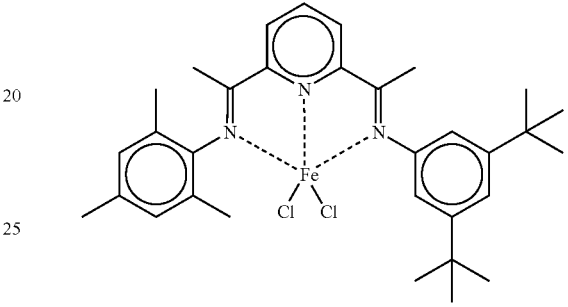

In an inert atmosphere a solution of 400 mg diimine (0.855 mmol) in 20 ml dichloromethane was added to 100 mg FeCl$_2$ (0.789 mmol) in 30 ml dichloromethane. The mixture was stirred for 16 hours. A small amount of precipitate was removed by centrifugation. Pentane (40 ml) was added to the solution. The blue precipitate was isolated by filtration and dried in vacuo. Yield 0.420 g (90%) of iron complex. $^1$H-NMR (Cl$_2$CDCDCl$_2$, broad signals) δ 78.6 (1H, Py-H$_m$), 76.8 (1H, Py-H$_m$), 29.7 (1H, Py-H$_p$), 20.9 (3H, Me), 18.3 (6H, Me), 15.2 (2H, ArH), 0.7 (18H, Bu$^t$), − 4.1 (3H, MeC=N), −11.5 (1H, ArH), −15.6 (2H, o-ArH), −30.7 (3H, MeC=N).

Alternatively the catalyst used in the oligomerisation experiments below was 2-[1-(2,4,6-trimethylphenylimino) ethyl]-6-[1-(4-eicosanoxy-3,5-diphenylphenylimino)ethyl] pyridine iron [II] chloride complex which was prepared according to the method described below:

Preparation of 4-hydroxy-3,5-diphenylacetanilide

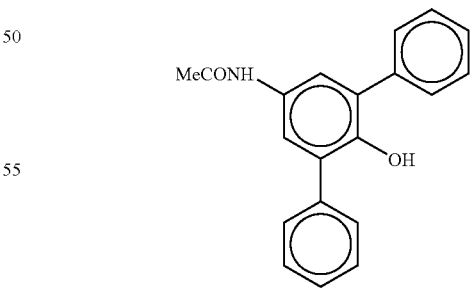

To 4-hydroxy-3,5-diphenylaniline (4 g, 15.3 mmol) in 30 ml of ethanol was added 1.6 ml of acetic anhydride. The reaction was stirred for 16 hours. The resulting mixture was poured into water. The pink product (6 g) was isolated by filtration, washed with water, dried and used without further purification. $^1$H-NMR (CDCl$_3$, selected data) δ 5.31(s, OH), 2.16 (s, Me).

Preparation of 4-eicosanoxy-3,5-diphenylacetanilide

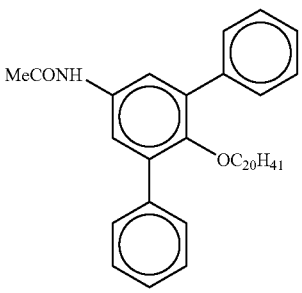

A mixture of 4-hydroxy-3,5-diphenylacetanilide (6 g), 1-bromoeicosane and 10 g potassium carbonate was refluxed in acetone (70 ml) for 16 hours. The reaction mixture was poured into water. The product was isolated by filtration, washed with water and dried. Crystallisation from pentane yielded 7.2 g of 4-eicosanoxy-3,5-diphenylacetanilide as a white solid. $^1$H-NMR (CDCl$_3$, selected data) δ 3.13(t, CH$_2$O), 2.17 (s, Me).

Preparation of 4-eicosanoxy-3,5-diphenylaniline

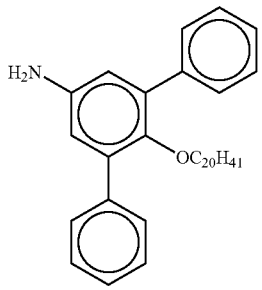

To 4-eicosanoxy-3,5-diphenylacetanilide (7.2 g) was added 24 g NaOH in 30 ml H$_2$O and 40 ml ethanol. The resulting mixture was refluxed for 16 hours. The reaction mixture was poured on ice. The product was isolated by filtration and washed with water. Crystallisation from ethanol yielded 5.9 g (10.9 mmol) of 4-eicosanoxy-3,5-diphenylaniline as a white solid. $^1$H-NMR (CDCl$_3$) δ 7.27–7.63 (m, 10H, ArH), 6.67 (s, 2H, ArH), 3.60 (br s, 2H, NH$_2$), 3.09 (t, 2H, CH$_2$O), 0.8–1.4 (m, 39H, alkyl).

Preparation of 2-[1-(2,4,6-trimethylphenylimino)ethyl]-6-[1-(4-eicosanoxy-3,5-diphenylphenylimino)ethyl]pryridine

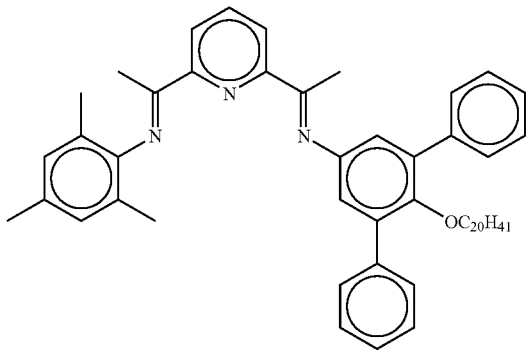

2-[1-(2,4,6-trimethylphenylimino)ethyl]-6-acetyl pyridine (3 g, 10.7 mmol), prepared according to the method disclosed in WO02/28805, and 4-eicosanoxy-3,5-diphenylaniline (5.8 g, 10.7 mmol) were dissolved in 200 ml of toluene. To this solution, 4 Å molecular sieves were added. After standing for 1 day the mixture was filtered. The solvent was removed in vacuo. The residue was crystallised from cold ethanol. The product was isolated as a yellow treacle (6.5 g, 8.1 mmol, 76%) after drying at 60° C. in vacuo. $^1$H-NMR (CDCl$_3$) δ 8.45 (d, 1H, Py-H$_m$), 8.37 (d, 1H, Py-H$_m$), 7.89 (t, 1H, Py-H$_p$), 7.67 (d, 4H, ArH), 7.1–7.5 (m, 16H, ArH), 6.90 (s, 2H, ArH), 6.86 (s, 2H, ArH), 3.19 (t, 2H, CH$_2$O), 2.51 (s, 3H, Me), 2.29 (s, 3H, Me), 2.22 (s, 3H, Me), 2.01 (s, 6H, Me), 0.8–1.4 (m, 39H, alkyl).

Preparation of 2-[1-(2,4,6-trimethylphenylimino)ethyl]-6-[1-(4-eicosanoxy-3,5-diphenylphenylimino)ethykl]pyridine iron[II] chloride complex

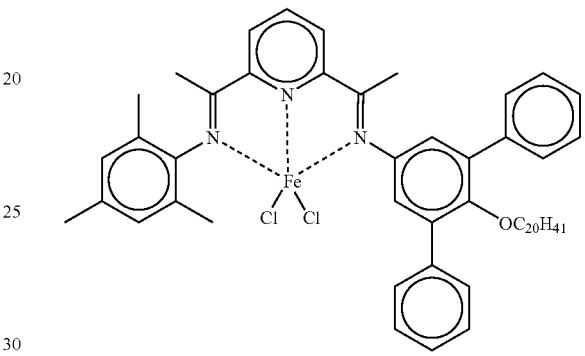

In an inert atmosphere a solution of 5 g above-described diimine in 20 ml dichloromethane was added to 788 mg FeCl$_2$ in 30 ml dichloromethane. The mixture was stirred for 16 hours. The solution was filtrated. The solvent was removed in vacuo. The resulting green blue product was washed with pentane, isolated by filtration and dried in vacuo. Yield 5 g (86%) of iron complex. $^1$H-NMR (CD$_2$Cl$_2$, broad signals, selected data) δ 81.4 (1H, Py-H$_m$), 80.5 (1H, Py-H$_m$), 21.1 (3H, Me), 17.3 (6H, Me), 16.0 (2H, ArH), 0.21 (3H, Me), −13.8 (2H, ArH), −30.4 (3H, Me).

Alternatively, any of the catalyst compounds prepared in WO02/28805, WO 02/00339, WO01/58874 or WO 03/011876 could be used in the oligomerisation experiments below.

The first co-catalyst compound used in the experiments below was modified methyl aluminoxane (MMAO) wherein about 25% of the methyl groups are replaced with isobutyl groups. MMAO-3A in heptane ([Al]=6.42% wt) used in Examples 1–19 of Table 1, was purchased from AKZO-NOBEL Chemicals B.V., Amersfoort, The Netherlands. In the 0.5 liter autoclave experiments, (entries 20 and higher of Table 1) methyl aluminoxane (MAO) in toluene was used supplied under the tradename Eurecen AL 5100/10T, batch: B7683; [Al]=4.88% wt, TMA=35.7 wt % (calculated), molecular mass=900 g/mol and [Al]=4.97% wt) supplied by Witco GmbH, Bergkamen, Germany.

The second co-catalyst compound used in the oligomerisation experiments below was neat zinc diethyl supplied by Ethyl Corporation, Baton Rouge, LA, U.S.A.

Catalyst System Preparation

In a Braun MB 200-G dry box the 2-[1-(2,4,6-trimethylphenylimino)ethyl]-6-[1-(4-tert-butylphenylimino)ethyl] pyridine iron[II] chloride complex, the 2,6-bis[1-(2,6-difluorophenylimino)ethyl]pyridine iron [II] chloride complex, the 2-[1-(2,4,6-trimethylphenylimino)ethyl]-6-[1-(3,5-ditert-butylphenylimino)ethyl]pyridine iron[II] chloride complex or the 2-[1-(2,4,6-trimethylphenylimino)ethyl]-6-[1-(4-eicosanoxy-3,5-diphenylimino)ethyl]pyridine iron (II) complex (typically about 22.5 µmol) was placed in a glass bottle sealed by a septum; toluene (typically about 10 ml) was added. The resulting mixture was stirred for several hours. This yielded a finely divided coloured suspension. In the case of the 2-[1-(2,4,6-trimethylphenylimino)ethyl]-6-[1-(4-eicosanoxy-3,5-diphenylphenylimino)ethyl]pyridine iron (II) chloride complex a clear dark-green solution in toluene was obtained instantaneously. Part of this suspension or solution was used in the oligomerisation reaction.

Oligomerisation Experiments in Endeavor Unit

Oligomerisation experiments were carried out in an Endeavor® (Argonaut Technologies), a device with eight separately heated and pressurised 20 ml stainless steel reactors. Each reactor is equipped with a glass liner, stirrer and injection port.

In order to remove traces of water from the reactor, it was flushed three times with dry nitrogen at 150° C. Then the reactor was flushed with ethylene at room temperature. Subsequently, 2 ml of toluene with the appropriate amounts of MMAO and $Et_2Zn$ (Table 1) were added through the injection port of the reactor. The reactor was heated to the desired temperature (Table 1) and pressurised with ethylene to the pressure indicated in Table 1. A suspension of the iron complex was injected through the injection port (typical amount: 0.45 µmol in 0.2 ml toluene). The stirring at 500 rpm was continued under constant ethylene pressure for at least 2 h. After this period the feed supply closed, stirring stopped, and the reactor cooled down automatically. After cooling to room temperature the ethylene was vented with air and n-hexylbenzene (45 mg, internal standard) in 0.2 ml toluene was injected through the injection port of the reactor to the crude product. The glass liner was removed from the reactor. The amount and purity of olefins were determined by gas chromatography. The data are reported in Table 1.

Oligomerisation Experiments in a 0.5-Liter Autoclave Oligomerisation experiments were carried out in a 0.5 liter steel autoclave equipped with jacket cooling with a heating/cooling bath (ex. Julabo, model no. ATS-2) and a turbine/gas stirrer and baffles.

In order to remove traces of water from the reactor, it was evacuated overnight at <10 Pa, at 70° C. The reactor was scavenged by introducing 250 ml toluene, MAO (0.3 g solution) and subsequent stirring at 70° C. under nitrogen pressure of 0.4–0.5 MPa for 30 min. The reactor contents were discharged via a tap in the base of the autoclave. The reactor was evacuated to 0.4 kPa and loaded with 125 ml toluene and heated to the temperature indicated in Table 1 (entries 20 and higher) and pressurised with ethylene to the pressure indicated in Table 1.

The MAO-solution (typically 140 mg) and zinc diethyl (typically 10 mg) were then added to the reactor with the aid of toluene (the total volume injected was 30 ml, using a procedure similar to the injection of the catalyst solution; see below) and the stirring at 800 rpm was continued for 30 minutes.

0.40 µmol of the catalyst system prepared as described above was introduced into the stirred reactor using an injection system with the aid of toluene (the total volume injected was 30 ml: the catalyst solution diluted with toluene to 10 ml was injected and the injector system was rinsed twice with 10 ml toluene).

The addition of the catalyst system resulted in an exotherm (generally 5–25° C.), which generally reached a maximum within 1 minute and was generally followed by establishment of the temperature and pressure indicated in Table 1 (entries 20 and higher).

After consuming a certain volume of ethylene, the oligomerisation was stopped by rapid venting of the ethylene, decanting the product mixture into a collection bottle using a tap in the base of the autoclave. Exposure of the mixture to air resulted in rapid deactivation of the catalyst.

After addition of n-hexylbenzene (0.5–3.5 g) as internal standard to the crude product, the amount and purity of $C_6$, $C_8$ and $C_{10}$ olefins was determined by gas chromatography. The data are reported in Table 1 (entries 20 and higher).

From the experimental data provided in Table 1 it can be seen that there are a number of benefits from replacing some of the MMAO or MAO co-catalyst with zinc diethyl. There is a significant increase in the selectivity of linear alpha olefins (as measured by the % purity) and the amount of unwanted (methyl-) branched by-product is reduced. Whilst the selectivity to linear alpha olefins is increased the total olefin yield remains at least on a par with that of the experiments without zinc diethyl addition, as is clear from the yield of $C_6$, $C_8$ and $C_{10}$ oligomers (amount of $C_6$, $C_8$ and $C_{10}$ product measured in mg) of entries 1–19 of Table 1.

TABLE 1

Experiments in Endeavor unit using 0.45 µmol 2-[1-(2,4,6-trimethylphenylimino) ethyl]-6-[1-(4-tert-butylphenylimino) ethyl] pyridine iron[II] chloride system or in 0.5-litre autoclave (entries 20 and higher) using 0.40 µmol alternate Fe-catalyst systems.

| Example No. (* = comparative example) | Co-catalyst | | Process Conditions | | C6 products | | | C8 products | C10 products | | |
|---|---|---|---|---|---|---|---|---|---|---|---|
| | MMAO (eq.) | ZnEt2 (eq.) | T (° C.) | P (bara) | mg | Purity % | Me-br % | mg | mg | Purity % | Me-br % |
| 1 | 50 | 125 | 50 | 19 | 66 | 96.1 | 0.5 | 58 | 47 | 92 | 0.6 |
| 2 | 100 | 100 | 50 | 19 | 174 | 96.4 | 2.2 | 150 | 118 | 92.3 | 4.8 |
| 3 | 100 | 125 | 50 | 19 | 191 | 97.5 | 0.6 | 170 | 140 | 94.0 | 0.9 |
| 4 | 100 | 150 | 50 | 19 | 181 | 95.1 | 2.2 | 155 | 128 | 86.7 | 4.3 |
| 5 | 125 | 75 | 50 | 19 | 152 | 94.8 | 3.6 | 130 | 106 | 88.8 | 7.7 |
| 6 | 125 | 175 | 50 | 19 | 253 | 94.2 | 2.7 | 217 | 171 | 85.7 | 5.3 |
| 7 | 250 | 125 | 50 | 19 | 272 | 96.5 | 2.4 | 240 | 182 | 92.9 | 4.3 |
| 8*) | 100 | 0 | 50 | 19 | 77 | 86.9 | 7.1 | 61 | 47 | 70.5 | 14.9 |
| 9*) | 150 | 0 | 50 | 19 | 74 | 86.1 | 6.9 | 58 | 45 | 72.4 | 13.3 |
| 10*) | 200 | 0 | 50 | 19 | 114 | 88.4 | 7.2 | 93 | 70 | 72.9 | 12.0 |
| 11*) | 250 | 0 | 50 | 19 | 125 | 90.6 | 4.9 | 106 | 84 | 77.6 | 9.9 |

TABLE 1-continued

Experiments in Endeavor unit using 0.45 μmol 2-[1-(2,4,6-trimethylphenylimino) ethyl]-
6-[1-(4-tert-butylphenylimino) ethyl] pyridine iron[II] chloride system or in 0.5-litre
autoclave (entries 20 and higher) using 0.40 μmol alternate Fe-catalyst systems.

| Example No. (* = comparative example) | Co-catalyst | | Process Conditions | | C6 products | | | C8 products | C10 products | | |
|---|---|---|---|---|---|---|---|---|---|---|---|
| | MMAO (eq.) | ZnEt2 (eq.) | T (° C.) | P (bara) | mg | Purity % | Me-br % | mg | mg | Purity % | Me-br % |
| 12*) | 500 | 0 | 50 | 19 | 101 | 92.5 | 5.3 | 90 | 70 | 84.8 | 9.9 |
| 13 | 100 | 100 | 100 | 19 | 134 | 93.0 | 5.0 | 110 | 84 | 83.6 | 11.5 |
| 14 | 125 | 175 | 100 | 19 | 132 | 93.2 | 3.2 | 116 | 86 | 79.3 | 7.7 |
| 15 | 125 | 175 | 100 | 26 | 140 | 94.9 | 1.9 | 118 | 88 | 85 | 3.9 |
| 16 | 250 | 175 | 100 | 26 | 82 | 93.3 | 4.2 | 63 | 46 | 87.9 | 9.1 |
| 17 | 110 | 140 | 100 | 31 | 45 | 96.9 | 1.0 | 41 | 35 | 96.9 | 0.9 |
| 18 | 110 | 140 | 100 | 31 | 54 | 96.8 | 1.1 | 45 | 34 | 96.4 | 1.5 |
| 19*) | 250 | 0 | 100 | 31 | 57 | 94.0 | 3.5 | 47 | 35 | 89.2 | 8.1 |
| 20*)**) | 700***) | 0 | 70 | 16 | 24670 | 93.4 | 3.4 | 12770 | 6040 | 87.1 | 11.3# |
| 21*)**) | 900***) | 0 | 70 | 16 | 7350 | 92.7 | 5.1 | 3680 | 1780 | 83.2 | 14.6# |
| 22**) | 600***) | 300 | 70 | 16 | 8490 | 97.7 | 1.2 | 4650 | 2350 | 94.4 | 5.1# |
| 23*)##) | 700***) | 0 | 50 | 16 | 10320 | 97.8 | 1.8 | 9560 | 8200 | 93.5 | 5.8# |
| 24*)##) | 1000***) | 0 | 50 | 16 | 8530 | 98.1 | 1.5 | 7880 | 6660 | 94.4 | 5.1# |
| 25##) | 400***) | 700 | 50 | 16 | 11580 | 99.0 | 0.8 | 10930 | 9090 | 96.5 | 3.2# |
| 26*)$) | 900***) | 0 | 50 | 16 | 5470 | 98.7 | 1.0 | 4580 | 3630 | 96.5 | 3.2# |
| 27$) | 600***) | 300 | 50 | 16 | 3720 | 99.9 | 0.1 | 3400 | 2930 | 99.5 | 0.5# |

*)Comparative Experiment.
**)Using 2,6-bis[1-(2,6-difluorophenylimino)ethyl]pyridine iron[II] chloride complex.
***)Using MAO instead of MMAO.
)Total branched decenes.
)Using 2-[1-(2,4,6-trimethylphenylimino)ethyl]-6-[1-(3,5-di-tert-butylphenylimino)ethyl]pyridine iron[II] chloride complex.
$)Using the soluble 2-[1-(2,4,6-trimethylphenylimino)ethyl]-6-[1-(4-eicosanoxy-3,5-diphenylphenylimino)ethyl) pyridine iron (II) chloride complex

We claim:

1. A catalyst system comprising:
   (a) one or more bisarylimino pyridine iron or cobalt catalysts;
   (b) a first co-catalyst compound which is selected from aluminium alkyls, aluminoxanes, and mixtures thereof; and
   (c) a second co-catalyst compound which comprises one or more compounds of the formula $ZnR'_2$ wherein each R', which may be the same or different, is selected from hydrogen, optionally substituted $C_1-C_{20}$ hydrocarbyl, phenyl, F, Cl, Br, I, SR", $NR''_2$, OH, OR", CN, NC wherein R", which within the same molecule may the same or different, is $C_1-C_{20}$ hydrocarbyl.

2. The catalyst system of claim 1 wherein R' is $C_1-C_{20}$ hydrocarbyl.

3. The catalyst system of claim 2 wherein R' is $C_1-C_{20}$ alkyl.

4. The catalyst system of claim 3 wherein R' is $C_1-C_6$ alkyl.

5. The catalyst system of claim 4 wherein R' is ethyl.

6. The catalyst system of claim 1 wherein the first co-catalyst is an aluminoxane selected from the group consisting of methyl aluminoxane, alkyl-modified methyl aluminoxane, and mixtures thereof.

7. The catalyst system of claim 6 wherein the first co-catalyst is an isobutyl-modified methyl aluminoxane.

8. The catalyst system of claim 1 wherein the molar ratio of the metal of the first co-catalyst to the metal of the second co-catalyst is in the range of from about 5:1 to about 1:5.

9. The catalyst system of claim 8 wherein molar ratio is from about 3:1 to about 1:3.

10. The catalyst system of claim 9 wherein molar ratio is from about 2:1 to about 1:2.

11. The catalyst system of claim 1 wherein the bisarylimino pyridine iron or cobalt catalyst is selected from the group consisting of bisaryliminepyridine $MX_n$ complexes and/or [bis-aryliminepyridine $MY_p.L_b^+$] $[NC^-]_q$ complexes, said bis-aryliminepyridine complexes comprising a bisarylimine pyridine ligand, wherein M is a metal atom selected from the group consisting of Fe or Co, n is 2 or 3, and X is halide, optionally substituted hydrocarbyl, alkoxide, amide or hydride, Y is a ligand which may insert an olefin, $NC^-$ is a non-coordinating anion, p+q is 2 or 3, matching the formal oxidation of said metal atom; L is a neutral Lewis donor molecule; b is 0, 1 or 2.

12. The catalyst system of claim 11 wherein the bisarylimine pyridine ligand is selected from the group consisting of ligands having the formula (I) below:

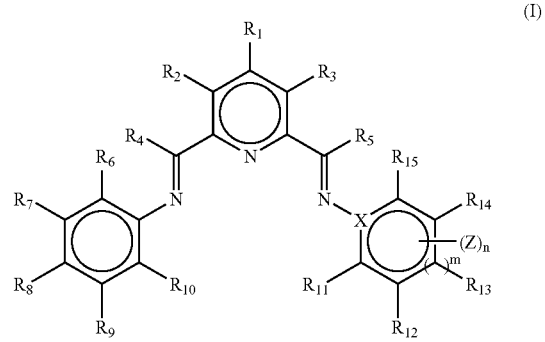

(I)

wherein X is carbon or nitrogen,
n is 0 or 1,
m is 0 or 1,

Z is a π-coordinated metal fragment, $R_1$–$R_5$, $R_7$–$R_9$ and $R_{12}$–$R_{14}$ are each, independently, hydrogen, optionally substituted hydrocarbyl, an inert functional group, or any two of $R_1$–$R_3$, $R_7$–$R_9$ and $R_{12}$–$R_{14}$ vicinal to one another taken together may form a ring; $R_6$ is hydrogen, optionally substituted hydrocarbyl, an inert functional group, or taken together with $R_7$ or $R_4$ to form a ring; $R_{10}$ is hydrogen, optionally substituted hydrocarbyl, an inert functional group, or taken together with $R_9$ or $R_4$ to form a ring; $R_{11}$ is hydrogen, optionally substituted hydrocarbyl, an inert functional group, or taken together with $R_5$ or $R_{12}$ to form a ring; and $R_{15}$ is hydrogen, optionally substituted hydrocarbyl, an inert functional group, or taken together with $R_5$ or $R_{14}$ to form a ring.

13. A process for the production of alpha-olefins comprising reacting ethylene under oligomerisation conditions in the presence of an effective amount of the catalyst system of claim 1.

14. The process of claim 13 wherein the reaction temperature is from about −100° C. to about 300° C.

15. The process of claim 14 wherein the reaction temperature is from about 0° C. to about 200° C.

16. The process of claim 15 wherein the reaction temperature is from about 50° C. to about 150° C.

17. The process of claim 13 wherein the reaction pressure is from about 0.1 to about 15 mPa.

18. The process of claim 17 wherein the reaction pressure is from about 1 to about 10 mPa.

19. The process of claim 18 wherein the reaction pressure is from about 1.5 to about 5 mPa.

20. The process of claim 13 wherein the conditions are selected to produce a product slate having a K-factor of about 0.40 to about 0.90.

21. The process of claim 20 wherein the conditions are selected to produce a product slate having a K-factor of about 0.60 to about 0.80.

* * * * *